United States Patent [19]
Greco et al.

[11] 3,960,969
[45] June 1, 1976

[54] METHOD FOR PREPARING AN IMPROVED CREOSOTE WOOD PRESERVATIVE FROM A COAL TAR CREOSOTE BY THE USE OF CAUSTIC COMPOUNDS

[75] Inventors: Nicholas P. Greco, Pittsburgh; David A. Webb, Valencia, both of Pa.

[73] Assignee: Koppers Company, Inc., Pittsburgh, Pa.

[22] Filed: Feb. 7, 1975

[21] Appl. No.: 547,860

[52] U.S. Cl. .......................... 260/627 H; 260/621 R; 208/2
[51] Int. Cl.² ................. C07C 39/06; C07C 37/28
[58] Field of Search ........ 260/621 R, 621 A, 621 H, 260/627 R, 627 H, 627 G; 208/2; 23/237, 239

[56] References Cited
UNITED STATES PATENTS 2,040,100   5/1936   Miller ..................................... 208/2
2,044,764   6/1936   Bywater ................................. 208/2

*Primary Examiner*—James O. Thomas, Jr.
*Assistant Examiner*—W. B. Lone
*Attorney, Agent, or Firm*—Oscar B. Brumback; Herbert J. Zeh, Jr.

[57] ABSTRACT

An improved creosote wood preservative that has a light color and that forms a non-sticky crud deposit is prepared from a coal tar creosote. The coal tar creosote is distilled to an end temperature in the range of 395° to 410°C. at atmospheric pressure. This distillation produces a distillate and a pitch residue. The distillate is contacted with at least 1% by weight of one or more of the following caustic compounds: alkali metal alcoholates of alkali metal hydroxides to produce the improved creosote wood preservative. The pitch residue from distillation is recovered and it is utilized in the production of various pitch products or in combustion for its fuel value.

17 Claims, No Drawings

METHOD FOR PREPARING AN IMPROVED CREOSOTE WOOD PRESERVATIVE FROM A COAL TAR CREOSOTE BY THE USE OF CAUSTIC COMPOUNDS

BACKGROUND OF THE INVENTION

This invention relates to a method of preparing an improved creosote wood preservative from coal tar creosote. More particularly, this invention relates to a method of preparing an improved creosote wood preservative that has a more stable, and lighter color than coal tar creosote and that does not form a sticky crud deposit like coal tar creosote.

Creosote has been used to preserve wood from decay and biological attack for many years. Creosote has been used to preserve, almost indefinitely, railroad crossties, wood blocks and timbers for buildings, tanks, bridges, telephone and telegraph and utility poles, crossarms, fence posts, and marine and foundation pilings and the like. Creosote consists principally of liquid and solid aromatic hydrocarbons. A more precise definition of creosote is that it consists of the 200° – 400°C. boiling fraction of the distillate produced by the high temperature carbonization of bituminous coal. The main constituents of creosote have been classified by W.P.K. Findlay in "Preservation of Timber," Adams and Charles Black, London, 1962 as: (1) tar acids such as phenol, cresol, and xylenol, etc., and (2) tar bases such as pyridine, quinoline and acridine, and (3) neutral oils, such as a mixture of naphthalene, anthracene, and other neutral hydrocarbons.

Although creosote is an excellent wood preservative, it has several disadvantages. One disadvantage is that it has a dark color which is imparted to the treated wood. The color may become darker after exposure of the treated wood to air and light. A second disadvantage is that the creosote has a tendency to form a sticky crud deposit on the treated wood after the treated wood is exposed to sunlight. Crud is a black sticky substance that can be defined chemically as the carbon disulfide insolubles of creosote after the creosote is exposed to ultraviolet radiation. After creosote is applied to a wooden pole, such as a utility pole, the pole is protected from decay and biological attack but the pole may have a blackish color and deposits of a black sticky substance, crud, often appear after exposure to sunlight.

The Cleveland Electric Illuminating Company has set color specifications, C.E.I. color specifications, for treated wood utility poles. These specifications set in the year 1965 and identified as Ser. No. 073 run from a value of 1 for a light colored treated wood to a value of 9 for black colored treated wood pole. The other values between 1 and 9 are 3, 5, and 7 and they indicate an increased darkening color of the creosote treated wood. To meet the requirements of the utility company, the creosote treated wood must have a C.E.I. value of 5 or less. Wood specimens treated with a conventional creosote have a C.E.I. value of 8.

One method used in the prior art to lighten the color of creosote is discussed in U.S. Pat. No. 3,046,217, W.F. Hefner et al. In this method the conventional creosote is heated to a temperature of about 100° to 150°C. While the creosote is maintained at this temperature, it is aerated for a period of about one hour. The easily oxidized compounds in the creosote are oxidized to stable oxidation products. Then, the air blown creosote is distilled to a temperature of about 395° to 410°C. at atmospheric pressure. The purified light colored creosote is the distillate from the distillation step and the oxidized products remain behind in the residue. Next, the distillate is cooled to a temperature of about 40°C. to form crystals rich in anthracene, phenanthrene and carbazole. These crystals are removed from the distillate and the completed purified light colored creosote preservative is recovered.

There is a need in the art for a method of producing a light creosote wood preservative that imparts its light color to the treated wood and retains its light color after prolonged exposure to air and light. There is also a need in the art for a method of producing a light colored creosote wood preservative that does not form a sticky crud on the treated wood after the treated wood is exposed to sunlight.

SUMMARY OF THE INVENTION

The object of this invention is to provide a method of preparing an improved creosote wood preservative which imparts a stable light color to treated wood and which does not form a sticky crud deposit on the treated wood after the treated wood is exposed to sunlight.

In accordance with the present invention a method of preparing an improved creosote wood preservative is provided wherein a coal tar creosote is distilled to an end temperature equivalent to a temperature in the range of 395° to 410°C. at atmospheric pressure to produce a distillate and a pitch residue. Then, at least 1% by weight of one or more of the caustic compounds selected from the group consisting of alkali metal alcoholates or alkali metal hydroxides is contacted with the distillate before it comes in contact with air or light to produce the improved creosote wood preservative. These caustic compounds may be used with any solvent in which the caustic compound is soluble and that is soluble in the distillate. Examples of solvents are water, alcohol, glycol, cellosolves and the like. The pitch residue from distillation is recovered and if any inorganic contaminants are present the pitch is neutralized and water washed to remove them. It can be used directly in the production of various pitch products or in combustion for its fuel value.

The improved creosote wood preservative contains anthracene and penanthrene and carbazole which form crystals in the preservative at a temperature below 40°C. These compounds may be removed from the improved creosote wood preservative or allowed to remain in the improved creosote wood preservative. In order to keep these compounds in solution, the improved creosote wood preservative may be diluted with 20 to 25% by weight of a correction oil before it is used to impregnate the wood. This correction oil is a low boiling solvent mixture of methylnaphthalenes and a solvent that is compatible with both methylnaphthalenes and the distillate or improved creosote wood preservative. This correction oil may be added to the distillate before the distillate is contacted with the caustic compound or the correction oil may be added to the improved creosote wood preservative.

DETAILED DESCRIPTION OF THE INVENTION

The process of this invention is performed either in a batch or in a continuous operation. When the process of this invention is conducted in a continuous operation, it is preferred to adapt the process of this invention to existing creosote producing plants.

Any coal tar creosote may be used in the process of this invention. Examples of conventional coal tar creosotes, which can be used, are American WoodPreservers' Association standard creosote P1-65, P7-72, and P13-65. These standard creosotes are also cited in the United States Federal Standards TT-C-645B and TT-C-655(1). Also a coal tar creosote which has been subjected to heating, aeration or refluxing may be used as the starting coal tar creosote for the process of this invention. It is preferred to use a coal tar creosote that has been treated to remove some of the easily removable tar acids. This treatment reduces the quantity of caustic compound needed for the contacting of the distillate. Such a coal tar creosote would contain tar bases, neutral oils and some tar acids, some 60% of these components are volatile and have been characterized by gas chromatographic analysis. The compounds in weight percent are:

| | | | |
|---|---|---|---|
| Naphthalene | 3.0 | Phenanthrene | 11.4 |
| Methylnaphthalenes | 1.2 | Anthracene | 3.0 |
| Diphenyl | 0.1 | Carbazole | 5.7 |
| Dimethylnaphthalenes | 1.6 | Methylphenanthrenes | 2.3 |
| Acenaphthene | 5.5 | Fluoranthrene | 5.9 |
| Dibenzofuran | 3.0 | Pyrene | 8.1 |
| Fluorene | 6.0 | Benzofluorene | 2.2 |
| Methylfluorenes | 1.4 | | |

In addition, the tar acids of the creosote may consist of the following in weight percent: 2, 3 and 3, 5 xylenol (7.7); 2, 3, 6 trimethylphenol (4.3); 3,4 xylenol and 2, 4, 6 trimethylphenol (3.7); pentamethylbenzene (1.1); 2, 3, 5 and 2, 4, 5 trimethylphenol (1.0); 2, 6 xylenol (0.4); 2, 4 and 2, 5 xylenol (0.3). It is believed that some of these tar acids, mainly the phenolic compounds, which have a tendency of darkening on oxidation, may be largely responsible for the discoloration of the creosote.

The coal tar creosote is introduced into a distillation vessel for simple, fractional or vacuum distillation. Any distillation vessel known to those skilled in the art that separates the distillate from the residue may be used. The coal tar creosote is distilled to an end temperature equivalent to a temperature in the range of 395° – 410°C at atmospheric pressure. It is most preferred to vacuum distill the creosote to a temperature around 300°C at a reduced pressure of around 60 mm. This distillation produces a light colored distillate and a soft solid pitch residue.

The light colored distillate still contains phenolic compounds that would darken on contact with air or light. When this clear light distillate was applied to a wood test block and subjected to stability tests, it gave a Cleveland Electric Illuminating Company (C.E.I.) color value of 8. Therefore, before the distillate comes in contact with air or light, it is contacted with at least 1% by weight of an alkali metal alcoholate or alkali metal hydroxide. This contacting is performed in any vessel known to those skilled in the art that has an agitating device and that in some way precludes the admission of air and light or that allows the immediate contact between the distillate and the caustic compound after distillation occurs. The contacting occurs with agitation and at any temperature within the range from the melting temperature to the boiling temperature of the creosote.

In the preferred embodiment of the invention an alkali metal alcoholate is used to contact the distillate and this alcoholate can be either in a solid or in a liquid state. It is preferred to use the alcoholate in the liquid state by dissolving a solid alkali metal alcoholate in a non-aqueous solvent that is soluble in creosote. The solvent can be the alcohol of the alcoholate or a cellosolve or any solvents within which both the alcoholate and the creosote are soluble. It is preferred to use sodium methylate as the alcoholate and perferably it is dissolved in methanol or methyl cellosolve.

After the sodium methylate is contacted with the distillate, the distillate darkens and there is an evolution of methanol. It is believed, but not a limitation on the process of this invention, that the alkali metal, here sodium is distributed throughout the distillate by the alkali metal alcoholate, here sodium methylate. Then, the alcohol, here methanol, evaporates and the alkali metal, here sodium, reacts with the phenolic compound to form salts. These salts are soluble within the distillate but they do not darken when the distillate is contacted by air or light. This distillate with the phenolic compounds dissolved within it as sodium salts is the improved creosote wood preservative. When this improved creosote wood preservative is used in a mixture with pentachlorophenol to treat wood, it is considered advantageous to have the sodium phenolate salts in the improved creosote wood preservative. These salts reduce the amount of corrosion which might occur from the use of pentachlorophenol. These phenolic salts also may be removed from the improved creosote wood preservative by crystallization or any other method known to those skilled in the art.

In an alternative embodiment of this invention an alkali metal hydroxide is used to contact the distillate. This alkali metal hydroxide is preferably sodium hydroxide which can contact the distillate either in a solid or in a liquid state but preferably in a liquid state. For this liquid state at least 1 weight percent of the sodium hydroxide is dissolved in an aqueous solution. It is believed, without limiting the process of this invention, that the sodium hydroxide reacts with the phenolic compounds in the tar acids of the coal tar creosote to form sodium phenolic salts. These salts remain soluble in the distillate and they do not darken when the distillate is exposed to light and air. This distillate containing the dissolved sodium phenolate salts is the improved creosote wood preservative. Also, the distillate may be treated to remove these sodium phenolic salts and this distillate would constitute the improved creosote wood preservative. This treatment may be any treatment for removing dissolved salts from a liquid and known to those skilled in the art.

In order to assure that none of the compounds of the improved creosote wood preservative, namely anthracene, phenanthrene and carbazole, crystalize at low temperatures around 40°C., a correction oil is added. The correction oil, which is a mixture of methylnaphthalenes and a solvent that is compatible with the methylnaphthalene and the distillate is preferably added in an amount of 20 – 25% by weight to the improved creosote wood preservative. Another manner of preventing these compounds from forming crystals in the improved creosote wood preservative is to remove them. This is accomplished by cooling the improved creosote wood preservative below 40°C., crystallizing these compounds and separating them from the improved creosote wood preservative.

The improved creosote wood preservative was tested in laboratory stability and accelerated aging tests. The stability tess include impregnating a wood test block with the improved creosote wood preservative and then exposing the test block to conditions that simulate plant storage. Conditions used to simulate plant storage are a temperature of 160°F. or 71°C. at a residence time of 16 hours followed by 8 hours at 25°C. with exposure to air. This procedure is repeated three times for a total of 72 hours. The resulting color of the block is measured by visual comparison with a Ser. No. 073, 1965, Cleveland Electric Illuminating Company (C.E.I.) color specification chart. In the accelerated aging tests a southern yellow pine sapwood containing both spring and summer growth, cut into blocks having the dimensions of 2 ×2 ×½ inches, is soaked with the improved creosote wood preservative containing a correction oil at 80°C. for 20 minutes until about 2 grams of the improved creosote is absorbed. This absorbed amount is equivalent to the normal amount of conventional creosote absorbed per foot of wood. Then the block is irradiated with ultraviolet radiation in air with a 325 watt Hanovia high pressure mercury ultraviolet lamp for 72 hous at hours 80°F. or 27°C. to simulate outdoor exposure conditions. After exposure, the color of the block is measured by visual comparison with the Ser. No. 073, 1965, C.E.I. color chart. Such a test proved that the wood block impregnated with the improved creosote wood preservative had a C.E.I. value of 5 or less.

EXAMPLE I

In this and following examples a coal tar creosote, hereinafter referred to as Creosote A, was used as the starting coal tar creosote for the production of the improved creosote wood preservative. Creosote A has the following characteristics:

| | | |
|---|---|---|
| Moisture content | 0.2% | by volume |
| Specific gravity | 1.106 | |
| Composition in percent by weight on a water-free basis in the following boiling fractions: | | |
| Up to 210°C. | 0.0 | |
| Up to 235°C. | 0.0 | |
| Up to 270°C. | 5.4 | |
| Up to 315°C. | 28.0 | |
| Up to 355°C. | 62.8 | |
| Residue content | 37.0 | wt. % |

One hundred grams of Creosote A was heated to 300°C. at an atmospheric pressure and maintained at this reflux temperature for 5 minutes. The refluxed Creosote A was then distilled at 60 mm pressure to an end vapor temperature of 300°C. This distillation produced 18 grams of residue and 81.5 grams of a light colored distillate to which correction oil was added. Sodium methylate in the amount of 1.5 grams in a 25% methanol solution was stirred into the corrected distillate at 70°C. and the distillate darkened immediately with evolution of methyl alcohol. The corrected distillate is a distillate to which correction oil has been added. A wood test block treated with this improved creosote wood preservative gave a C.E.I. value of 4.

EXAMPLE II

The same procedure was used in Example I wherein the distilled Creosote A was treated with 1% sodium methylate and gave a C.E.I. value of 4.5. After stability tests the wood treated with this improved creosote wood preservative gave a C.E.I. value of 5.

TABLE 1

Table 1 presents data on the treatment of Creosote A with the caustic compounds of this invention to obtain a creosote with a light color. This light colored creosote is the improved creosote wood preservative of this invention. The Table indicates the caustic compounds used, and the C.E.I. color value before a stability test and after a stability test. Runs No. 3 and No. 6 show that a quantity of caustic compound less than 1% by weight is not sufficient to interact with the phenolic compounds in the distillate.

| The Treatment of Creosote A With Caustic Compounds For The Improvement Of Color | | | |
|---|---|---|---|
| Run No. | Caustic Compound Used | C.E.I. | |
| | | Before Stability Test | After Stability Test |
| 1 | 1% sodium methylate | 3.5 | 5 |
| 2 | 1% sodium methylate | 4.0 | 5 |
| 3 | 0.43% sodium methylate in methanol | — | 6 |
| 4 | 1% sodium methylate | 4.5 | 5 |
| 5 | 1.5% sodium methylate in methanol | 4 | 5 |
| 6 | 0.5% NaOH in aq. soln. | 4.5 | 6 |

According to the provisions of the patent statutes, the principal, preferred construction and mode of operation of the invention have been explained and what is considered to represent its best embodiment has been illustrated and described. However, it should be understood that within the scope of the appended claims, the invention may be practiced otherwise than as specifically illustrated and described.

We claim:

1. A method of preparing an improved creosote wood preservative, having a lighter color and reduced tendency for formation of a crud deposit on treated wood, from a coal tar creosote comprising:
   a. distilling the coal tar creosote to an end temperature equivalent to a temperature in the range of 395° – 410°C at atmospheric pressure to produce a distillate and a pitch residue, and
   b. contacting the distillate with at least 1% by weight of a caustic compound selected from the group consisting of alkali metal alcoholates and alkali metal hydroxides and mixtures of alkali metal alcoholates and hydroxides at a temperature in the range from the melting temperature to the boiling temperature of the creosote whereby an improved creosote wood preservative is produced.

2. A method according to claim 1 wherein the coal tar creosote is distilled at a temperature of 300°C at a reduced pressure around 60 mm of mercury.

3. A method according to claim 1, wherein the coal tar creosote is refluxed to a temperature in the range of 250°C – 320°C at atmospheric pressure for a residence time of 5 – 60 minutes before the creosote is distilled.

4. A method according to claim 1 which includes recovering the pitch residue from distillation.

5. A method according to claim 1 which includes:
   a. adding a correction oil to the distillate before the distillate is contacted with the caustic compounds whereby anthracene, phenanthrene and carbazole are maintained in solution at low temperatures.

6. A method according to claim 1, which includes:
   a. adding a correction oil to the improved creosote wood preservative whereby anthracene, phenanthrene and carbazole are maintained in solution at low temperatures.

7. A method according to claim 1 wherein sodium methylate is used as the caustic compound.

8. A method according to claim 1 wherein sodium hydroxide is used as the caustic compound.

9. A method according to claim 1 which includes removing dissolved phenolate salts present in the improved creosote wood preservative.

10. A method according to claim 1 which includes removing anthracene, phenanthrene and carbazole from the improved creosote wood preservative.

11. A method of preparing an improved creosote wood preservative having a lighter color and reduced tendency for formation of crud deposit on treated wood from a coal tar creosote comprising:
   a. refluxing the coal tar creosote to a temperature in the range of 250°–320°C at atmospheric pressure for a residence time of 5 – 60 minutes
   b. distilling the refluxed creosote to an end temperature of 300°C at a reduced pressure around 60 mm of mercury to produce a distillate and a pitch residue, and
   c. contacting the distillate with at least 1% by weight of a caustic compound selected from the group consisting of alkali metal alcoholates, alkali metal hydroxides and mixtures of alkali metal alcoholates and hydroxides at a temperature in the range from the melting temperature to the boiling temperature of the creosote whereby an improved creosote wood preservative is produced.

12. A method according to claim 11 which includes adding a correction oil to the distillate before the distillate is contacted with the caustic compound whereby anthracene, phenanthrene and carbazole are maintained in solution at low temperatures.

13. A method according to claim 11 which includes adding a correction oil to the improved creosote wood preservative whereby anthracene, phenanthrene and carbazole are maintained in solution at low temperatures.

14. A method according to claim 11 which includes removing dissolved phenolate salts present in the improved creosote wood preservative.

15. A method according to claim 11 which includes removing anthracene, phenanthrene and carbazole from the improved creosote wood preservative.

16. A method according to claim 11 wherein sodium methylate is used as the caustic compound.

17. A method according to claim 11 wherein sodium hydroxide is used as the caustic compound.

* * * * *